United States Patent
Yu et al.

(10) Patent No.: US 10,711,313 B2
(45) Date of Patent: Jul. 14, 2020

(54) KIT FOR DETECTING CTDNA AND EXPRESSION OF DRUG-RESISTANT GENES RELATED TO APPLICABILITY OF TUMOR CHEMOTHERAPEUTIC DRUGS

(71) Applicants: GUIZHOU MEDICAL UNIVERSITY, Guiyang (CN); MATERNAL AND CHILD HEALTH HOSPITAL OF GUIYANG CITY, Guiyang (CN); GUIZHOU ENTRY-EXIT INSPECTION AND QUARANTINE BUREAU, Guiyang (CN)

(72) Inventors: Wenfeng Yu, Guiyang (CN); Shi Zhou, Guiyang (CN); Zhi Huang, Guiyang (CN); Bi Wang, Guiyang (CN); Rui Gao, Guiyang (CN); Dai Wei Zhao, Guiyang (CN); Hai Zhuang, Guiyang (CN); Ya Ling Liang, Guiyang (CN)

( * ) Notice: Subject to any disclaimer, the term of this patent is extended or adjusted under 35 U.S.C. 154(b) by 305 days.

(21) Appl. No.: 15/944,725

(22) Filed: Apr. 3, 2018

(65) Prior Publication Data

US 2019/0300961 A1 Oct. 3, 2019

(51) Int. Cl.
*C12Q 1/68* (2018.01)
*C07D 227/02* (2006.01)
*C12Q 1/6886* (2018.01)
*C12Q 1/686* (2018.01)
*C12Q 1/6869* (2018.01)

(52) U.S. Cl.
CPC ......... *C12Q 1/6886* (2013.01); *C07D 227/02* (2013.01); *C12Q 1/686* (2013.01); *C12Q 1/6869* (2013.01)

(58) Field of Classification Search
CPC .............................. C12Q 1/6886; C07D 227/02
USPC ......................................................... 435/6.14
See application file for complete search history.

(56) References Cited

FOREIGN PATENT DOCUMENTS

CN 101234112 B * 10/2010

OTHER PUBLICATIONS

Agata Głuszyńska International Journal of Biological Macromolecules 114, (2018) 479-490 (Year: 2018).*
Stratagene Catalog 1988, p. 39. (Year: 1988).*

* cited by examiner

*Primary Examiner* — Jezia Riley
(74) *Attorney, Agent, or Firm* — W&K IP

(57) ABSTRACT

A kit for determining ctDNA concentration and a method for determining ctDNA concentration is disclosed, wherein the method comprising dissolving extracted ctDNA in Tris-HCl buffer with pH>7.0 and adding into the buffer 2,7-bis(1-methyl-4-vinylpyridine)-9-ethylcarbazole iodised salt as a molecular probe, calculating the concentration of ctDNA in the solution by measuring the Fluorescence intensity of the solution. It has extremely high sensitivity in the determination of 0 μg/ml~50 μg/ml ctDNA solution.

7 Claims, 4 Drawing Sheets

KIT FOR DETECTING CTDNA AND EXPRESSION OF DRUG-RESISTANT GENES RELATED TO APPLICABILITY OF TUMOR CHEMOTHERAPEUTIC DRUGS

TECHNICAL FIELD

The present invention relates to the field of biotechnology, in particular to a kit for detecting ctDNA and the expression of drug-resistant genes related to the applicability of tumor chemotherapeutic drugs, a detection method and use thereof.

BACKGROUNDS ctDNA refers to free DNA released from primary tumor cells, circulating tumor cells in the blood circulation system and necrotic or apoptotic tumor cells to the peripheral blood. Tumor refers to abnormal cell lesions, not necessarily the lumps in the body. Such lesions make cells in part of the body have uncontrolled hyperplasia, assembled into lumps. ctDNA is a biomarker with both high sensitivity and specificity. ctDNA comes from genome mutation of tumor cells, the probability of false positives is low and the half-life is short, which can accurately reflect the current situation of the tumor. With the development of high-throughput sequencing and detection technology, the importance of ctDNA detection will also promote its clinical application. High-throughput sequencing, also known as Next-generation sequencing technology (NGS), can detect ctDNA in circulating blood with high sensitivity and high specificity. By ctDNA detection, traces of tumors in blood can be detected. ctDNA carries tumor-specific mutation fragments and shows the same biological characteristics as primary tumor tissues, such that the detection of ctDNA is relatively important for tumor metastasis and prognosis.

However, after ctDNA was extracted from peripheral blood, the detection of ctDNA concentration was to detect tumor-related gene loci in the tumor samples of patients with advanced cancer, analyze the hot spot mutated genes specific to the tumor tissue by gene sequence alignment, then detect trend in changes of mutated gene loci (ctDNA) in continuous blood samples of patients by using Digital PCR technology for the subsequent application of second-generation sequencing method.

After extracting ctDNA from peripheral blood, the rapid and simple detection of ctDNA concentration is of great significance for further understanding of the tumor and treatment thereof.

Clinical studies have shown that the expression of certain genes in tumor cells is related to the sensitivity of the chemotherapeutic drugs to tumor action and the degree of drug resistance. Different tumor cells have different sensitivity to the same drug, and also same tumor cell responds differently to different drugs.

Therefore, there proposed personalized treatment. This requires the detection of multiple genes expression, currently, most of the genes need to be detected individually, the operation is complex, the convenience is poor, it is difficult to set reference genes, and it has low throughput and high cost. For PCR amplification of multiple genes in a reaction system using multiple pairs of primers, that is, multiple gene detection, it requires to repeat optimal adjustment and verification for the amplification conditions and primers. The published simultaneous detection of multiple genes generally involves almost all of the commonly used detection genes without selection, including RRM1, TOP2A, ERCC1, TYMS, TUBB3, TOP1, PTEN, HER2, DPYD and EGFR. And it is only a one-time detection, the interpretations of the detection results are not relevant, some literatures published the so-called "personalized treatment" protocol, which is mainly to detect genes in low-level, for example, if TUBB3 exhibits low-level expression, paclitaxel or vinblastine drugs are selected, and if ERCC1 is expressed at low levels, cisplatin drugs are selected, but the indication of the detected genes that show high levels of expression is not clear.

SUMMARY OF THE INVENTION

In view of the above, in order to determine the concentration of ctDNA in a simple and convenient manner, an amphipathic compound 2,7-bis (1-methyl-4-vinylpyridine)-9-ethylcarbazole iodised salt (2,7-9E-BHVC) wherein carbazole is used as a parent core, and pyridine as an electronic receptor is disclosed herein, which is used as a molecular probe to detect the concentration of ctDNA.

The present invention provides a kit for measuring the concentration of ctDNA, comprising a compound 2,7-bis (1-methyl-4-vinylpyridine)-9-ethylcarbazole iodised salt as a molecular probe, the formula of the compound is

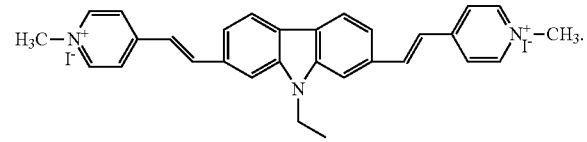 [SMILES: CCn1c2cc(/C=C/c3cc[n+](C)cc3)ccc2c2ccc(/C=C/c3cc[n+](C)cc3)cc21 ; [I-] ; [I-]]

According to an aspect of the present invention, the kit may further comprise Tris-HCl buffer of pH>7.0.

According to an aspect of the present invention, the buffer may be 10 mmol/L Tris-HCl buffer, pH=7.2.

According to an aspect of the present invention, the kit may further comprise an accelerator comprising the following components: 0.5 mM deoxynucleoside triphosphate, 2.8 mM potassium acetate, 120 mM UDP, 3 mM dihydronaphthylate, 0.2 mM triethyl iodide, 1.6 mM glycylglycine, 3.5 mM Eva Green, 5 mM Triton X-100, 1.5 mM dithiothreitol.

According to an aspect of the present invention, the accelerator may have a pH of 7.2.

The present invention further provides a method of determining ctDNA concentration comprising dissolving extracted ctDNA in Tris-HCl buffer of pH>7.0 and adding into the buffer 2,7-bis (1-methyl-4-vinylpyridine)-9-ethylcarbazole iodised salt as a molecular probe, calculating the concentration of ctDNA in the solution by measuring the Fluorescence intensity of the solution.

According to an aspect of the present invention, the buffer may be 10 mmol/L Tris-HCl buffer, pH=7.2.

According to an aspect of the present invention, the ctDNA concentration may be 0 μg/ml to 50 μg/ml.

According to an aspect of the present invention, in order to increase the speed of the assay, an accelerator may be added to the buffer, and the accelerator may contains the following components per 100 ml: 0.5 mM deoxynucleoside triphosphates, 2.8 mM potassium acetate, 120 mM UDP, 3 mM dihydronaphthylate, 0.2 mM triethyl iodide, 1.6 mM glycylglycine, 3.5 mM Eva Green, 5 mM Triton X-100, 1.5 mM dithiothreitol; the accelerator may be added earlier than the addition of the molecular probe 2,7-bis (1-methyl-4-vinylpyridine)-9-ethylcarbazole iodised salt with an interval of 30-120 s. After using the accelerator, the detection time can be shortened 1~1.3 h.

According to an aspect of the present invention, the accelerator may be added in an amount of 3 to 10% of the volume of the buffer.

DETAILED DESCRIPTION

Figure 1:
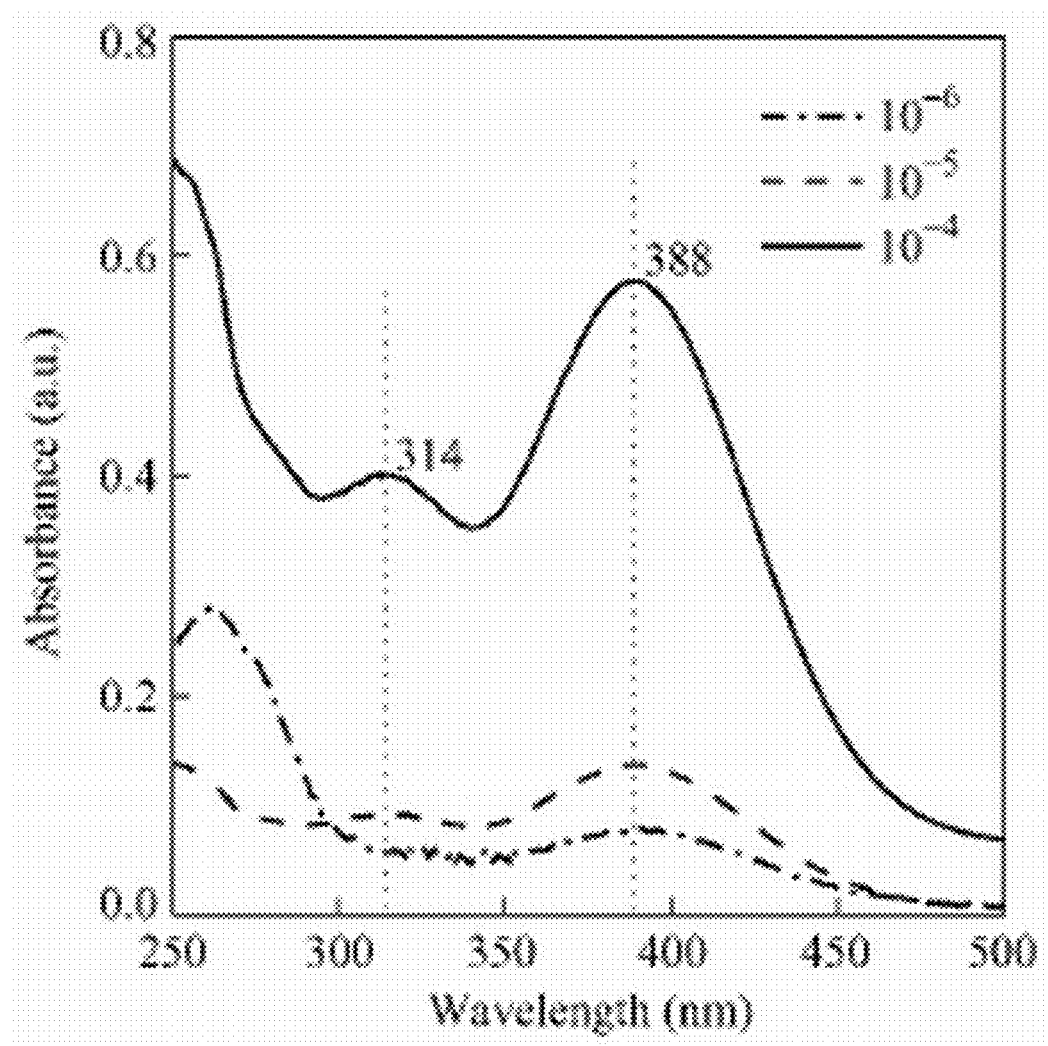
FIG. 1 UV-Vis spectra of BHVC in aqueous solution with different concentrations.

Synthesis of the Probe Compound 2,7-bis (1-methyl-4-vinylpyridine)-9-ethylcarbazole Iodised Salt of the Present Invention 4-Vinylpyridine, 4,4'-Difluorobiphenyl, 2-Iodoethanol were purchased from Acros Inc., Palladium acetate and Tri (o-tolyl) phosphine were purchased from Alfa Aesar and used directly without further purification and other reagents and solvents are domestic analytical grade, used in accordance with the solvent manual after purification. 1HNMR and 3CNMR of compounds were measured on a Bruker Avanace-300, 400 nuclear magnetic resonance spectrometers, and mass spectrometry and elemental analysis were performed on a LTQ Orbtrap XL and a Varian Cary 50 probe U V-visible spectrometer, respectively.

Fluorescence spectra were measured on a Perkin Elmer LS95, HITACH F-4500, and Edinburgh FLS920 fluorescence spectrometers at room temperature with laterally collection of fluorescence. Fluorescence lifetime was measured using the Edinburgh FLS920 fluorescence spectrometer. Two-photon fluorescence utilized laser pulses emitted by a Ti: sapphire Mira900-F mode-locked laser as the irradiation light source with a repetition frequency of 76 MHz and a pulse width of 200 fs using the SpectroPro 300i spectrometer to collect fluorescence laterally. The concentration of the sample in the measurement of the linear spectrum is in the order of $10^{-6}$ mol/L and the concentration of the sample in the nonlinear spectroscopy is in the order of $10^{-5}$ mol/L. All the test utilized 1.0 cm×1.0 cm Quartet pass quartz crystal cuvette. Reagents used to prepare solutions are either spectroscopic or chromatographic purified.

Example 1 Synthesis of Probe 2,7-9E-BHVC (Hereinafter Referred to as BHVC)

Synthesis of 1-nitro-4,4'-dibromobiphenyl

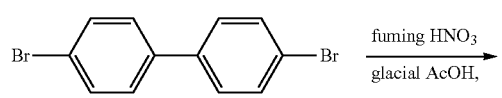

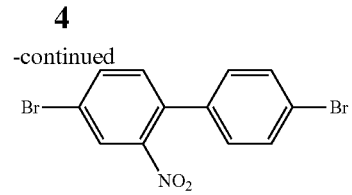

20 g (64 mmol) of 4,4'-dibromobiphenyl and 300 ml of glacial acetic acid was added to a 500 ml three-necked flask, heated to 100° C. with stirring, 100 ml 95% of fuming nitric acid was added dropwise, continued heating reaction for 30 min while maintaining the temperature at 100° C. After cooling and suction filtration, a yellow paste was obtained, which was recrystallized from ethanol to give 20.88 g of a yellow solid with a yield of 91.4%. ¹HNMR (300 MHz, CDCl₃) δ (ppm): 8.03 (d, J=1.8 Hz, 1H), 7.76 (dd, J=6.3 Hz, 2H), 7.56 (m, 2H), 7.3 (s, 1H), 7.16 (m, 2H).

Synthesis of 2,7-dibromo-9H-carbazole

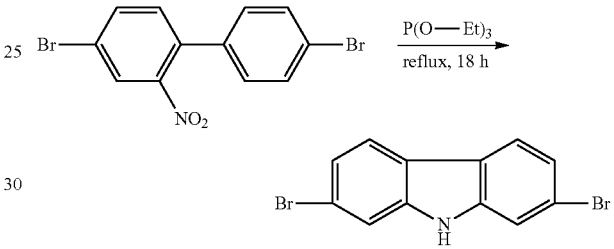

9 g (25.22 mmol) of 1-nitro-4,4'-dibromobiphenyl and 40 ml of triethylphosphite were added to a 100 ml three-necked flask, and the mixture was protected by argon and refluxed at about 150° C. for 18 h. The rest triethyl phosphate was removed by distillation under reduced pressure. The product was purified by column chromatography using n-hexane and ethyl acetate (20:1 by volume) as eluant to give 4.19 g of a white powder with a yield of 50%. ¹HNMR (400 MHz, Acetone), δ (ppm): 10.61 (S, 1H), 8.09 (d, J=8.4 Hz, 2H), 7.75 (d, J=8.4 Hz, 2H), 7.75 (d, J=1.7 Hz, 2H), 7.37 (dd, J=6.6 Hz, 2H).

Synthesis of 2,7-dibromo-9-ethylcarbazole

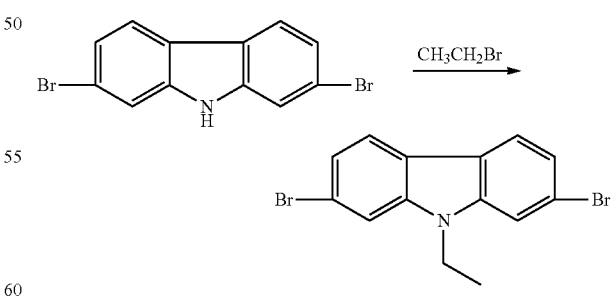

100 ml of DMF and 30 g of KOH were added to a 250 ml three-necked flask, and 5.0 g (15.4 mmol) of 2,7-dibromo-carbazole was further added, the mixture was stirred for 40 min and then 10 ml (134 mmol) of bromoethane was added dropwise, and was stirred at room temperature for 18 h. The reaction solution was poured into 1000 ml deionized water, a large number of white solid is precipitated, suction filtrated, the solid was washed with appropriate amount of ethanol three times, dried to give a white solid of 5.13 g, with a yield of 94.5%. $^1$HNMR (400 MHz, Acetone), δ (ppm): 8.11 (d, J=8.3 Hz, 2H), 7.84 (d, J=1.9 Hz, 2H), 7.39 (dd, J=6.6 Hz, 2H), 4.53 (dd, J=7.2 Hz, 2H), 1.44 (t, J=7.2 Hz, 3H).

Synthesis of 2,7-bis (4-vinylpyridine)-9-ethylcarbazole

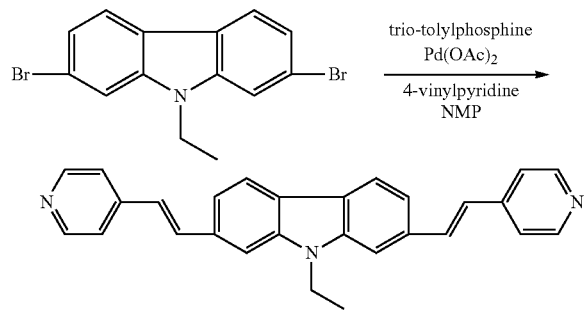

3.808 g (10 mmol) of 2,7-dibromo-9-ethylcarbazole was added to a 100 ml three-necked flask, 8.4 g (80 mmol) of 4-vinylpyridine was added dropwise, and 0.4954 g (1 mmol) of palladium acetate and 0.8731 g (3 mmol) of o-triphenylphosphine was used as catalysts, about 40 ml of NMP and 11.05 g (80 mmol) of potassium carbonate was added, and the temperature was slowly raised to 130° C. under the protection of argon and the reaction is continued at the temperature for 24 h, pouring into 500 ml of water after cooling, extracted with dichloromethane, the extracted solvent was evaporated to give a yellow solid, which was recrystallized from anhydrous ethanol to give a pale yellow solid of 0.77 g, with a yield of 53.1%. $^1$HNMR (400 MHz, CDCl$_3$), δ (ppm): 8.61 (d, J=6.0 Hz, 4H), 8.09 (d, J=8.1 Hz, 2H), 7.44-7.55 (m, 10H), 7.17 (d, J=16.2 Hz, 2H), 4.46 (dd, J=7.2 Hz, 2H), 1.53 (t, J=7.2 Hz, 3H).

Synthesis of 2,7-bis (1-methyl-4-vinylpyridine)-9-ethylcarbazole Iodised Salt (2,7-9E-BHVC)

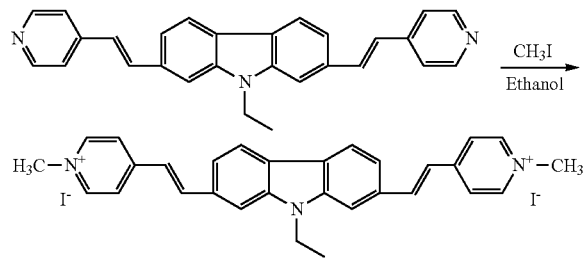

0.2048 g (0.51 mmol) of 2,7-bis (4-vinylpyridine)-9-ethylcarbazole and 0.2631 (1.53 mmol) of ICH2CH2OH were dissolved in ethanol in a 50 ml single neck flask, stirred at room temperature for 2 h, heated and refluxed 12 h to give an orange-red precipitate was suction filtered, washed three times with methanol to give an orange-red precipitation of 0.32 g, with a yield of 85%. $^1$HNMR (400 MHz, DMSO-d$_6$), δ (ppm): 8.90 (d, J=6.5 Hz, 4H), 8.23-8.32 (m, 8H), 8.09 (s, 2H), 7.74 (d, J=16.2 Hz, 2H), 7.68 (d, J=8.2 Hz, 2H), 5.28 (s, 2H), 4.58 (s, 6H), 3.88 (s, 4H), 1.45 (t, J=7.0 Hz, 3H). $^{13}$CNMR (100 MHz, DMSO-d$_6$), δ 53.6, 145.2, 142.4, 141.4, 134.1, 124.1, 123.8, 123.4, 121.9, 120.2, 109.8, 62.6, 60.5, 37.8, 14.4; HRMS (M/Z): [M-I]+ calcd for C$_{32}$H$_{33}$N$_3$I$_2$): C (51.56, 47.67), H (4.46, 4.35), N (5.64, 5.19).

Example 2 ctDNA Detection

First, a buffer solution of pH 7.2 is prepared, the preparation process of which is as follows: 394 mg of Tris-HCl and 1.863 g of KCl are added to a 250 ml beaker, and deionized water is added to prepare a buffer solution containing 10 mmol/L Tris-HCl and 100 mmol/L KCl and of pH 7.2 buffer solution.

Then, the buffer solution was used to prepare 0-500 μg/ml ctDNA aqueous solutions, wherein the BHVC content was maintained at $5\times10^{-6}$ mol/L.

Taking deionized water solution with ctDNA content of 100 μg/ml as an example, the specific preparation process is described as follows: First, 8.2 g compound BHVC was added to a 100 ml volumetric flask, followed by the addition of 100 ml pH 7.2 buffer solution to formulate to a BHVC buffer solution of concentration of $10^{-4}$ mol/L, then 1 ml the above solution was removed to dilute to 10 ml so that the concentration of BHVC was $10^{-5}$ mol/L, 5 ml of this solution was taken and added to a clean spawn bottle.

Then 10 mg ctDNA was taken and added to 10 ml volumetric flask, buffer was added to formulate as 100 μg/ml ctDNA solution, 1 ml this solution was taken, and then added to 4 ml buffer solution, the ctDNA concentration is diluted to 20 μg/ml, the ctDNA solution was added dropwise to the BHVC buffer solution previously placed in the spawn bottle under vigorous stirring. After the addition was completed, the ctDNA solution was allowed to stand still for 2 hours and its UV-Vis absorption and fluorescence spectra were measured.

The UV-vis absorption spectra of aqueous solutions of different concentrations of BHVC are shown in FIG. 1, the absorption peak at 688 mm is derived from the absorption of the two cross-shaped skeletons of BHVC, and the absorption peak at 314 mm is the characteristic absorption peak of tetraphenylethylene group. When the concentration of BHVC in aqueous solution changed from $10^{-6}$ mol/L to $10^{-4}$ mol/L, there was no red-shift or blue-shift of the UV absorption spectrum of the solution. In general, the shift of the absorption peak of the π-conjugated chromophore solution is due to the π-π interaction between the molecules. Therefore, the stability of the absorption spectrum shown in FIG. 1 shows that BHVC molecules have good solubility in aqueous solution, which is beneficial for the detection of water-soluble biological macromolecules such as DNA.

Figure 2:
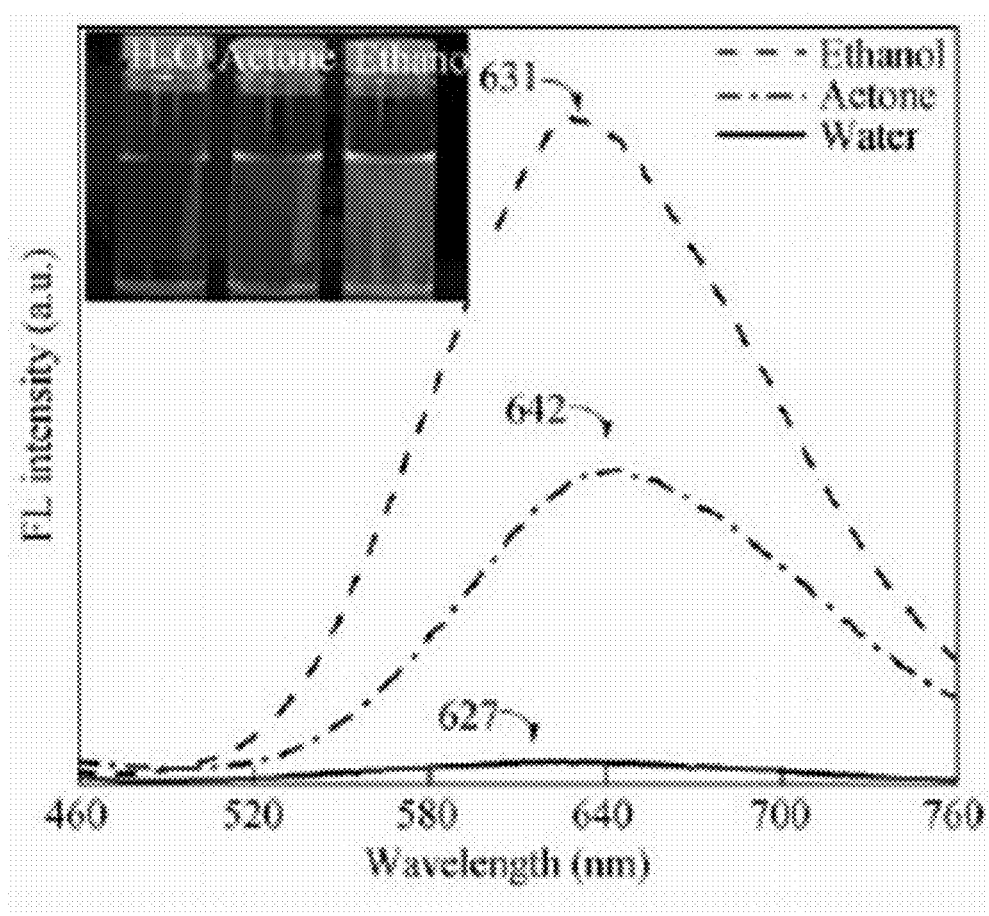
FIG. 2 Fluorescence spectra of BHVC in water, ethanol and acetone (10-5 mol/L), excitation wavelength: 420 nm. The inset shows the fluorescence images of the samples taken under 365 nm UV light.

The aqueous and ethanol solutions containing BHVC at a concentration of $10^{-5}$ mol/L were observed under a UV lamp and found that the basic luminescence in aqueous solution was very weak and red in ethanol solution. The fluorescence spectra of BHVC in aqueous and ethanol solution are shown in FIG. 2. It can be seen that the fluorescence intensity of BHVC in aqueous solution is very weak and the fluorescence emission peak is at 627 nm. However, the fluorescence intensity in ethanol solution with the same concentration of BHVC increases by 30 times, and the fluorescence emission peak red-shifted to 631 nm. In fact, ethanol is a poor solvent for BHVC. Therefore, BHVC exists in the form of aggregates in ethanol solvent. Fluorescence spectrum shows the luminescence of molecular aggregates. This shows that BHVC has typical aggregation-induced luminescence properties. To further demonstrate the aggregation-induced luminescence behavior of BHVC, a comparative test was conducted with another non-solvent acetone, and the fluorescence spectra are also given in FIG. 2. The results show that at the same concentration, BHVC exhibits significantly enhanced fluorescence emission than in aqueous solution and similar spectral red shift phenomenon to that in ethanol solvent, whereby demonstrating the aggregation-induced luminescence properties of BHVC.

For Detection of ctDNA Concentration

Figure 3:
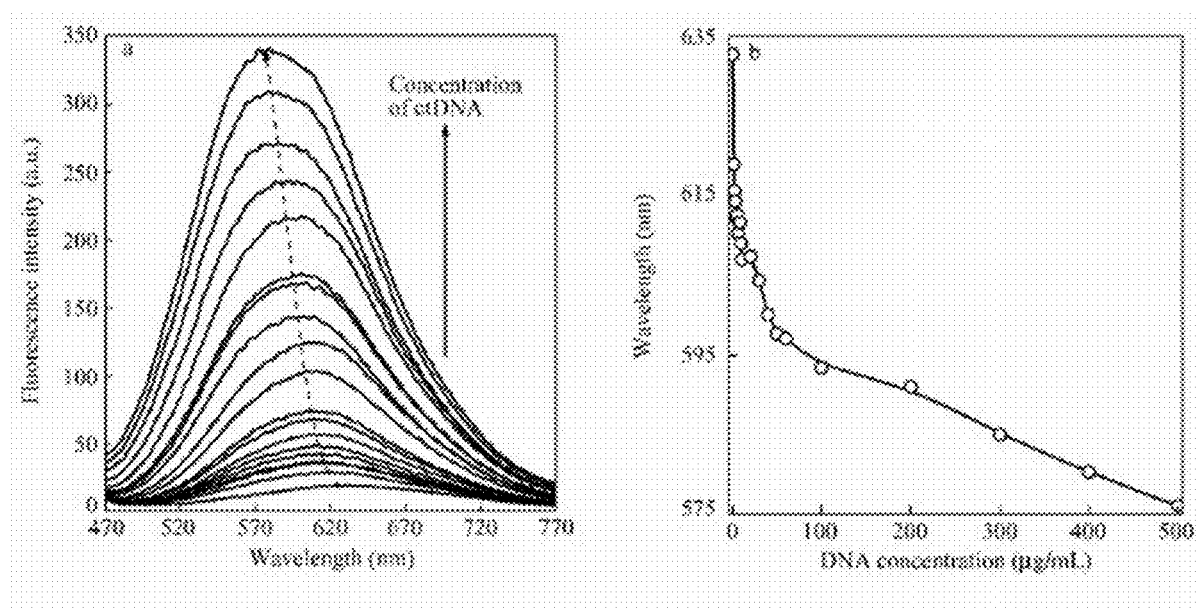
FIG. 3 (a) Variation of fluorescence spectra of BHVC in Tris-HCl buffer solution with different ctDNA concentrations; (b) Changes in peak wavelength of the fluorescence spectra with the variation of ctDNA concentration.

Based on the study of the absorption and aggregation-induced luminescence properties of BHVC, the fluorescence occurrence behavior of BHVC buffer solution with different ctDNA concentrations was studied with a buffer solution of pH 7.2 and containing 10 mmol/L Tris-HCl and 100 mmol/L KCl, the changes in the detected fluorescence spectrum are shown in FIG. 3 (a). It can be seen from the figure: as the ctDNA concentration increases, the fluorescence intensity of the solution gradually increases, and the fluorescence peak is blue-shifted. The results of quantitative test of the fluorescence spectrum shift are given in FIG. 3 (b). When the content of ctDNA changed from 0 μg/ml to 50 μg/ml, the maximum emission peak of fluorescence spectrum shifted from 633 nm to 598 nm, that is blue shifted 35 mm. When the ctDNA concentration was more than 50 μg/ml, the blue shift of the peak of the fluorescence spectrum appeared inflection point, the rate of change slowed down. When the ctDNA content was 500 μg/ml, the peak shifted to 576 nm, which was a blue shift of 24 nm relative to the fluorescence spectrum of a 50 μg/ml DNA solution (FIG. 3 (b)).

Figure 4:
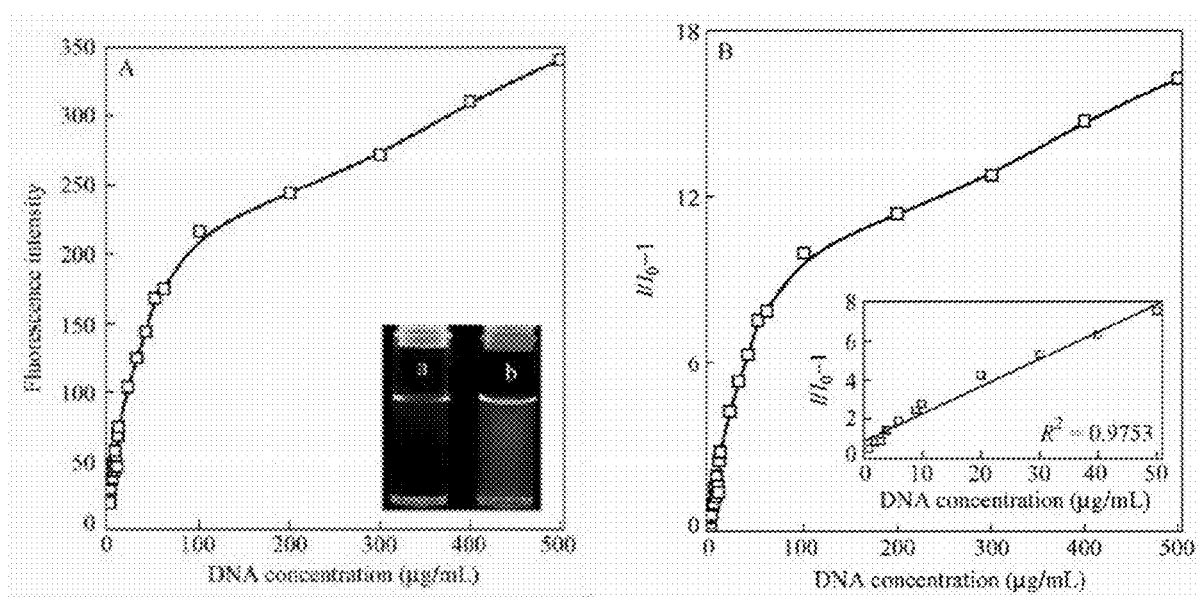
FIG. 4 (A) Variation of fluorescence intensity of BHVC with the concentration of ct DNA in Tris-HCl buffer solution (excitation wavelength: 420 nm). The inset shows the fluorescence images of the buffer solutions containing 0 μg/ml (a) and 50 μg/ml (b) ctDNA; (B) Stern-Volmer plot according to the data in (A). the inset displays the linear relationship between I/I0-1 versus DNA concentration in the region from 0 μg/ml to 50 μg/ml.

The trend in the change of fluorescence intensity of the solution is shown in FIG. 4 (A), with the ctDNA concentration increases, the fluorescence intensity of the solution can be divided into two intervals. The first interval was located at the concentration of 0 μg/ml to 50 μg/ml, wherein the change of the fluorescence emission peak intensity was relative intense; the second interval was where the ctDNA concentration was from 50 μg/ml to 500 μg/ml, wherein the change of the fluorescence intensity slowed down. Overall, the fluorescence intensity of a BHVC solution with a ctDNA concentration of 500 μg/ml increased 20-fold relative to that of the solution of 0 μg/ml concentration and strong orange-red fluorescence was clearly observed under UV light (FIG. 4 (A).

The sensitivity of the fluorescent probe relative to the analyte can be quantitatively studied by the Stern-Volmer equation $$I/I0=Ksv[Q]+1,$$

where I is the fluorescence intensity of the solution containing the analyte at a given concentration, $I_0$ is the fluorescence intensity of the solution without the analyte, [Q] is the concentration of the analyte, and Ksv is the Stern-Volmer constant, the larger the constant, the more sensitive the fluorescence probe. For BHVC, when the concentration of ctDNA was in the range of 0~50 μg/ml, the linear correlation between fluorescence intensity and ctDNA concentration was 0.9753, showing a good linear relationship (inset in FIG. 4 (B), which provides great convenience for the implement of detection. In this linear interval, Ksv is calculated by Stern-Volmer as $1.4 \times 10^2$. This Ksv value is relative high relative to the reported AIE compounds for detecting DNA concentrations. It is noted that, in the detection of ctDNA with BHVC as a fluorescent probe, not only significant fluorescence enhancement is observed but also significant spectral shift was observed at the same time. This means that one fluorescent probe can analyze and identify the tested species through two spectral indexes at the same time, which is equivalent to realizing double fluorescent labeling with one chromophore, which is of great significance in biological detection.

Example 3

On the basis of Example 2, 8 ml of accelerator was added and the pH of the accelerator was 7.2. The accelerator was added earlier than the addition of the molecular probe 2,7-bis (1-methyl-4-vinylpyridine)-9-ethyl carbazole iodised salt, and the time interval therebetween was 40 s. As a result, it was found that the detection time was shorter than that of Example 2 by 1.2 h, and the remaining detection results were the same as those in Example 2.

We claim:

1. A kit for measuring the concentration of ctDNA comprising a compound 2,7-bis (1-methyl-4-vinylpyridine)-9-ethylcarbazole iodised salt as a molecular probe, the formula of said compounds 2,7-bis (1-methyl-4-vinylpyridine)-9-ethylcarbazole iodised salt is as follows

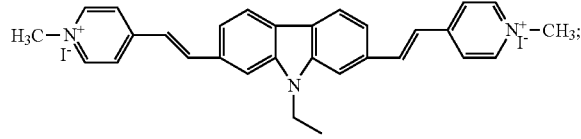

wherein, further comprising Tris-HCl buffer of pH>7.0;
wherein, the buffer is 10 mmol/L Tris-HCl buffer, pH=7.2;
wherein, further comprising an accelerator comprising the following components per 100 ml: 0.5 mM deoxynucleoside triphosphate, 2.8 mM potassium acetate, 120 mM UDP, 3 mM dihydronaphthylate, 0.2 mM triethyl iodide, 1.6 mM glycylglycine, 3.5 mM Eva Green, 5 mM Triton X-100, 1.5 mM dithiothreitol.

2. The kit according to claim 1, wherein the accelerator has a pH of 7.2.

3. A method of determining ctDNA concentration comprising dissolving extracted ctDNA in Tris-HCl buffer of pH>7.0 and adding to the buffer 2,7-bis (1-methyl-4-ethene Pyridyl)-9-ethylcarbazole iodised salt as a molecular probe, calculating the ctDNA concentration in the solution by measuring the Fluorescence intensity of the solution.

4. The method of claim 3, wherein the buffer is 10 mmol/L Tris-HCl buffer, pH=7.2.

5. The method according to claim 3, wherein the ctDNA concentration is 0 μg/ml to 50 μg/ml.

6. The method of claim 5, further comprising adding accelerator to the buffer comprising the following components per 100 ml: 0.5 mM deoxynucleoside triphosphates, 2.8 mM potassium acetate, 120 mM UDP, 3 mM dihydronaphthanate, 0.2 mM triethyl iodide, 1.6 mM glycylglycine, 3.5 mM Eva Green, 5 mM Triton X-100, 1.5 mM dithiothreitol; The addition of accelerator is earlier than that of the molecular probe 2,7-bis (1-methyl-4-vinylpyridine)-9-ethylcarbazole iodised salt, with an interval time therebetween of 30-120 s.

7. The method of claim 6, wherein the accelerator is added in an amount of 3 to 10% of the volume of the buffer.

* * * * *